United States Patent [19]

Olson et al.

[11] Patent Number: 6,101,413
[45] Date of Patent: Aug. 8, 2000

[54] CIRCUIT DETECTABLE PEDIATRIC DEFIBRILLATION ELECTRODES

[75] Inventors: Kenneth F. Olson, Minneapolis; Byron L. Gilman, Minnetonka; James E. Brewer, Cottage Grove, all of Minn.

[73] Assignee: SurVivaLink Corporation, Minneapolis, Minn.

[21] Appl. No.: 09/121,079

[22] Filed: Jul. 21, 1998

Related U.S. Application Data

[63] Continuation-in-part of application No. 08/658,200, Jun. 4, 1996, Pat. No. 5,817,151.

[51] Int. Cl.$^7$ .................................................. A61N 1/39
[52] U.S. Cl. ........................................ 607/5; 607/8
[58] Field of Search ............................... 607/5, 8

[56] References Cited

U.S. PATENT DOCUMENTS

| | | | |
|---|---|---|---|
| 4,494,552 | 1/1985 | Heath | 128/696 |
| 4,823,469 | 4/1989 | Broselow | 33/760 |
| 5,402,884 | 4/1995 | Gilman et al. | 206/328 |
| 5,562,710 | 10/1996 | Olsen et al. | 607/5 |
| 5,617,853 | 4/1997 | Morgan | 607/5 |
| 5,697,955 | 12/1997 | Stolte | 607/5 |
| 5,836,993 | 11/1998 | Cole | 607/59 |

FOREIGN PATENT DOCUMENTS

WO 94/26350  11/1994  WIPO.

OTHER PUBLICATIONS

Accurate Recognition and Effective Treatment of Ventricular Fibrillation by Automated External Defibrillators in Adolescents, Dianne L Atkins, Lori L. Hartley, Douglas K. York, Pediatrics, vol. 101, No. 3, Mar. 1998.

*Primary Examiner*—William E. Kamm
*Assistant Examiner*—Carl H. Layno
*Attorney, Agent, or Firm*—Patterson & Keough, P.A.

[57] ABSTRACT

Defibrillator electrodes having an identification element and a circuit which indicates to an AED the weight range of the patient being rescued. When the AED detects the presence of pediatric electrodes, it may select a different set of voice prompts that are specifically suited to a pediatric patient and/or it may select a pediatric dosage of electricity for the therapeutic shock.

37 Claims, 9 Drawing Sheets

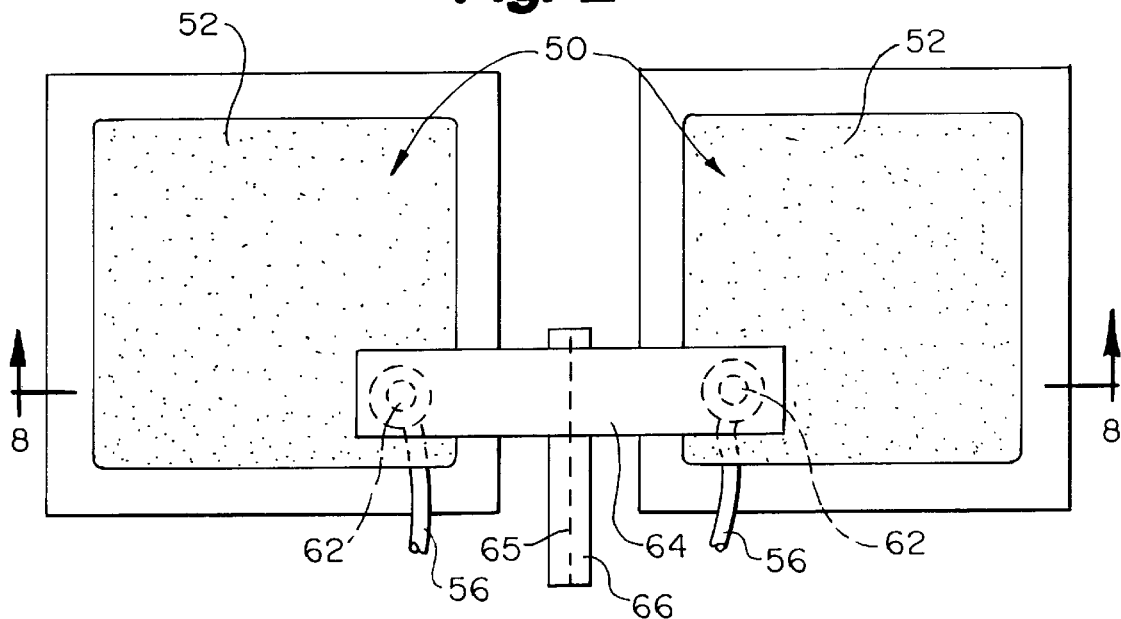
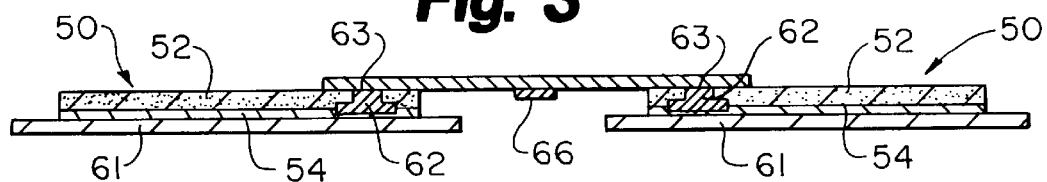
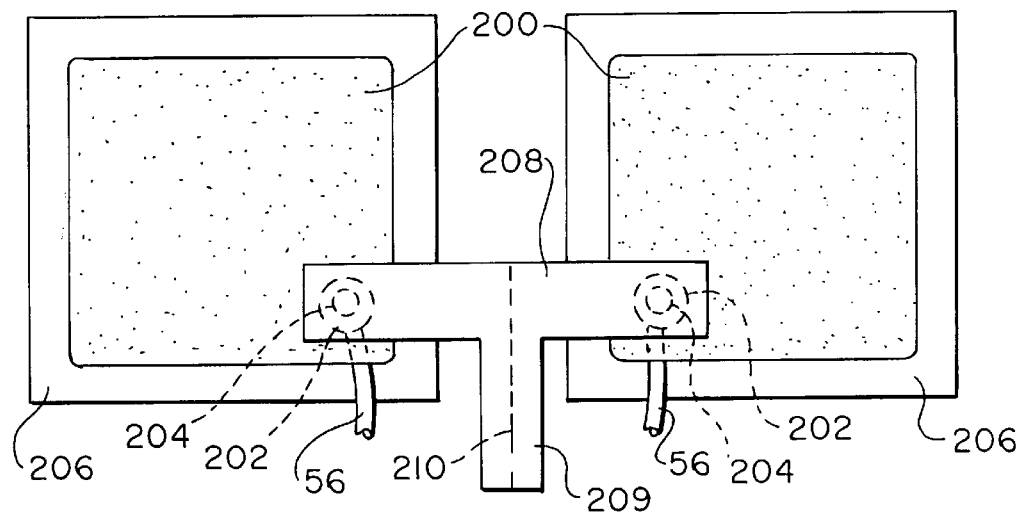

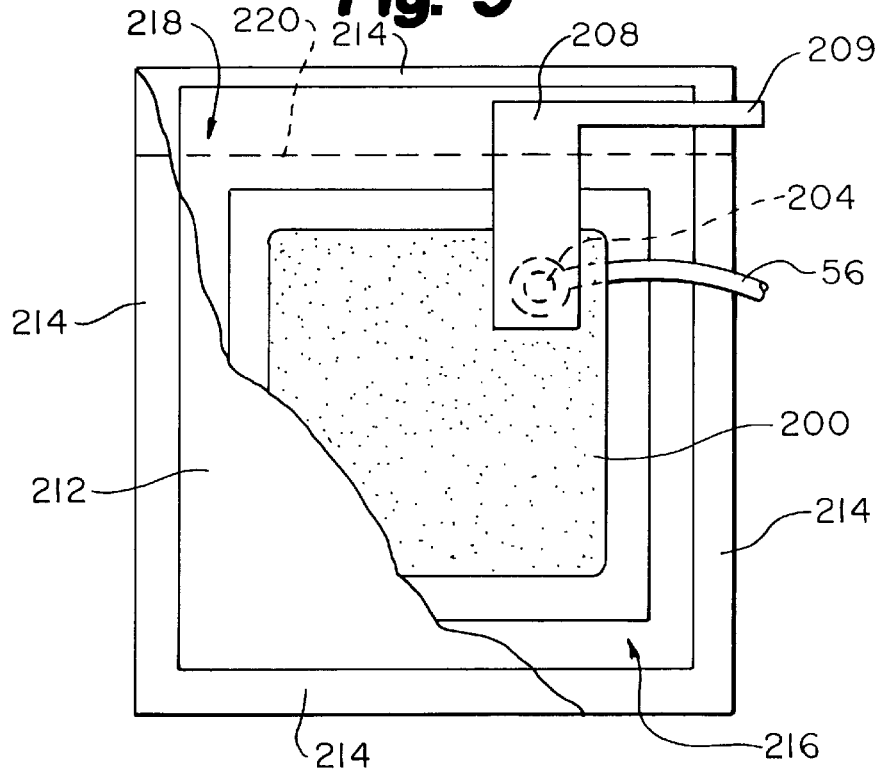
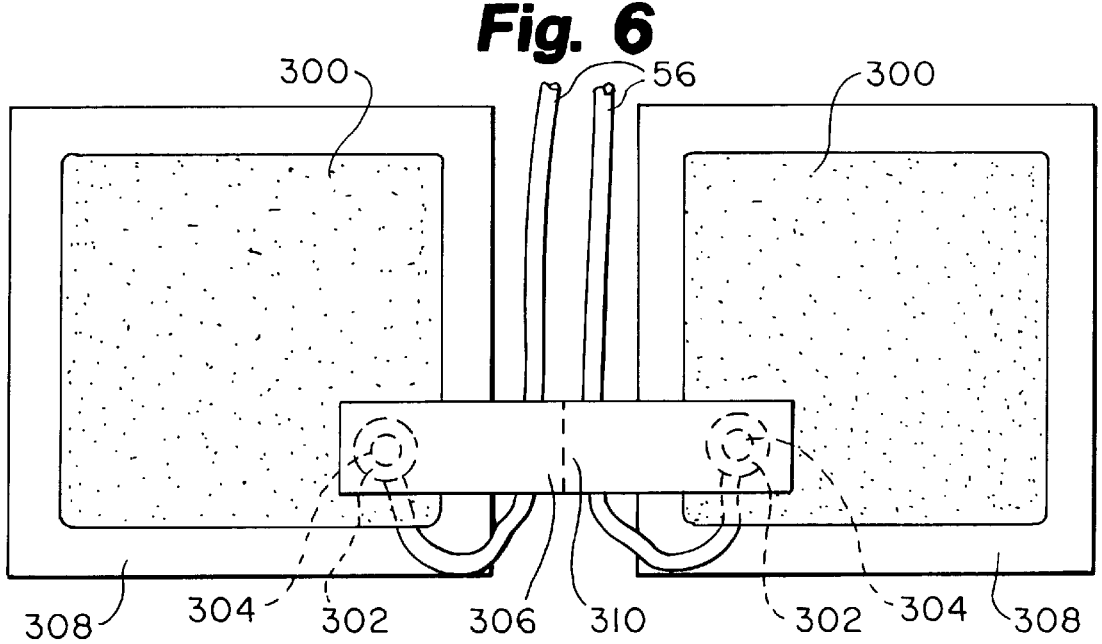

CIRCUIT DETECTABLE PEDIATRIC DEFIBRILLATION ELECTRODES

This application is a continuation-in-part of U.S. application Ser. No. 08/658,200 filed Jun. 4, 1996 now U.S. Pat. No. 5,817,151.

FIELD OF THE INVENTION

The present invention relates generally to electrotherapy methods and apparatus for delivering an electrical pulse to a patient's heart. More particularly the present invention relates to defibrillation electrodes for use with automatic external defibrillators (AEDs).

BACKGROUND OF THE INVENTION

Automatic External Defibrillators (AEDs) are used by first responders such as police officers, fire fighters, and emergency medical technicians to resuscitate victims of sudden cardiac arrest. These devices are designed to be simple to operate so they can be used by rescuers who do not have an extensive medical background, and who do not routinely defibrillate patients.

Studies have shown that the chances of successfully resuscitating a patient decrease approximately ten percent per minute following the onset of cardiac arrest. Accordingly, if an AED and a trained rescuer do not reach the patient in the first ten minutes, a victim of sudden cardiac arrest has nearly no chance of surviving. Because response time is critical, AEDs are currently being carried in emergency vehicles such as police cars and fire trucks. AEDs are also being widely deployed in areas where large numbers of people gather such as sports stadiums, gambling casinos, etc.

A significant limitation of the AEDs which have been deployed is that they can only be used on adult patients. Children who fall victim to cardiac arrest do not benefit from the wide deployment of AEDs, or the network of first responders who have been trained to operate AEDs. A pediatric patient must wait for a manual defibrillator and a doctor, nurse, or other professional who is qualified to operate a manual defibrillator.

SUMMARY OF THE INVENTION

The object of the present invention is overcome the limitations in the prior art by providing defibrillation electrodes intended for use with an AED to treat pediatric patients. By the arrangement of the electrodes and the package design of the present invention, the presence of pediatric electrodes can be detected by the AED and distinguished from electrodes intended for use with adult patients. When the AED detects the presence of pediatric electrodes, it may select a different set of voice prompts that are specifically suited to a pediatric patient and/or it may select a pediatric dosage of electricity for the therapeutic shock.

In accordance with one aspect of the present invention, a circuit detectable arrangement of a plurality of medical electrodes is provided with each electrode having an electrically non-conductive backing layer, a layer of electrically conductive adhesive disposed on the backing layer and a lead wire extending therefrom and electrically connected to the conductive adhesive. More specifically, a first electrode is disposed on an electrically non-conductive liner, a second electrode is disposed on an electrically non-conductive liner, and an electrical connector is provided between the first and second electrodes for electrically completing a circuit connecting the lead wire of the first electrode to the lead wire of the second electrode. Preferably, the backing layers of the first and second electrodes each include a conductor portion, and the electrical connector is connected between the conductor portion of the backing layer of the first electrode and the conductor portion of the backing layer of the second electrode. The electrical connector preferably comprises a strip of flexible and electrically conductive material and may include a non-conductive tear resistant strip.

In accordance with another aspect of the present invention, an electrode package is provided which is made of flexible material defining a pouch and having an interior cavity including first and second medical electrodes within an electrode receiving space therein. Moreover, in accordance with a package construction of the present invention, the lead wires from the first and second electrodes extend through an opening provided through the package to the outside of the package, and the package has a tear line along which the package is to be opened and which divides the interior cavity of the package into an electrode receiving space and an interior portion. Within the package, the first and second electrodes are provided adjacent to one another with their backing layers generally parallel to one another and with a loop formed in the electrical connector. The loop extends across the tear line and into the interior portion of the package so that by opening the package along the tear line, the electrical connector can be broken. The electrical connector may also include a strip of tear resistant material which is positioned within the interior portion of the package. Opening of the package can be facilitated by extending the strip of tear resistant material or a portion of the electrical connector through an opening of the package to provide a gripping means. Alternatively, at least one of the lead wires can be threaded within the package through the loop and within the interior portion so as to pass through the material of the packaging from the interior portion an provide an easy opening feature.

BRIEF DESCRIPTION OF THE DRAWINGS

FIG. 2 is a detailed plan view of unpackaged electrodes positioned on release liners.

FIG. 3 is a cross-sectional view through the pair of electrodes of FIG. 2 taken along line 3—3.

FIG. 4 is a detailed plan view of unpackaged electrodes in accordance with a second embodiment of the present invention.

FIG. 5 is a plan view of the electrodes of FIG. 4 folded one on top of the other and provided within a package shown partially broken away.

FIG. 6 is a detailed plan view of a pair of unpackaged electrodes in accordance with yet another embodiment of the present invention.

DETAILED DESCRIPTION OF THE PREFERRED EMBODIMENTS

The present invention is a circuit detectable pediatric defibrillation electrode and a package therefore. The present invention will be described and illustrated as being connected to an automated external defibrillator (AED) but it should be understood that the present invention is equally applicable to numerous other devices utilizing packaged electrodes.

Figure 1:
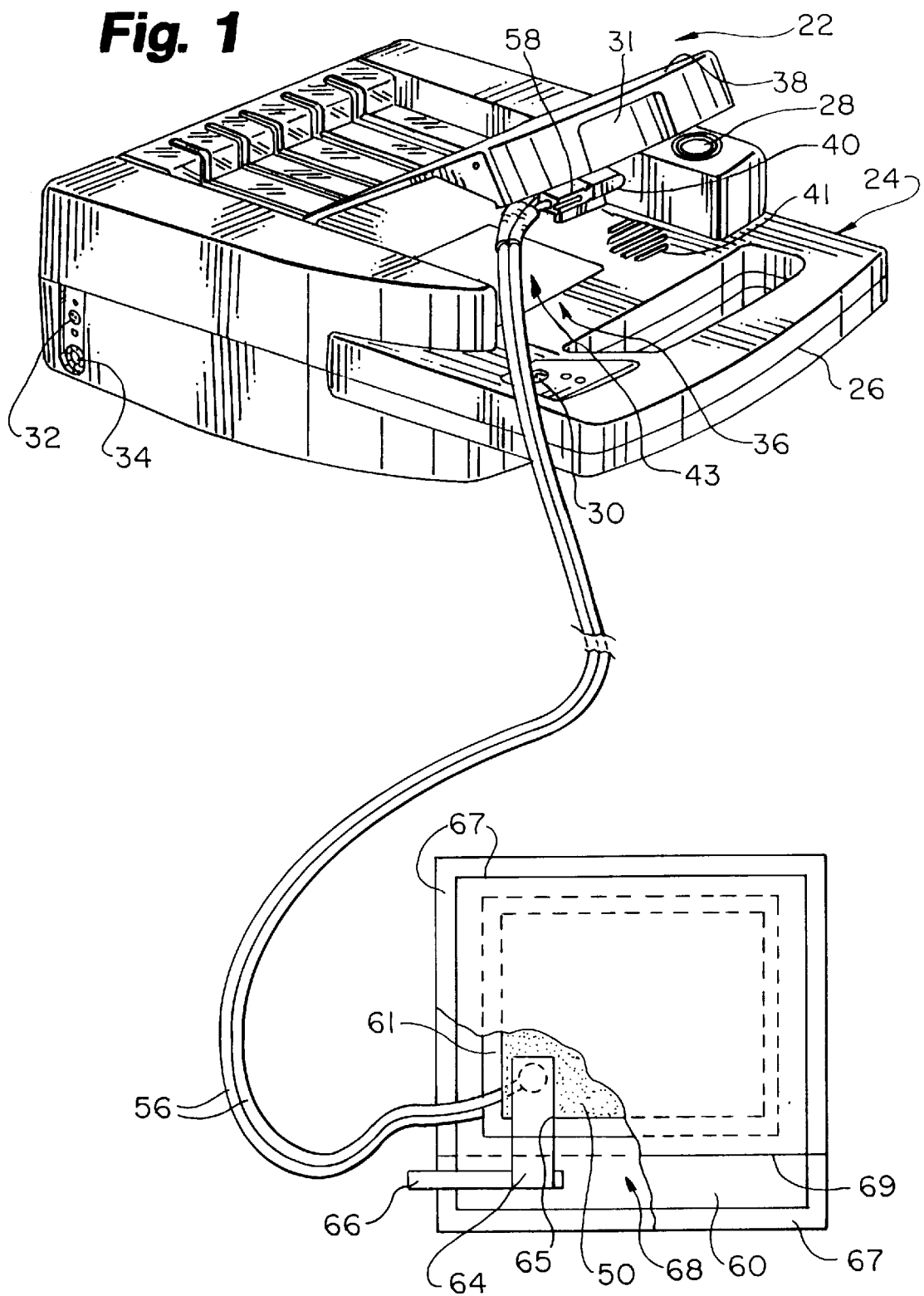
FIG. 1 is a perspective view of an AED.

FIG. 1 illustrates a pair of electrodes 50 connected to an AED 22. As can be seen in FIG. 1, defibrillator 22 includes plastic case 24 with a carrying handle 26 on the top portion. An illuminable rescue switch 28, visual maintenance indicator 30, data communication port 32 and charging port 34 are located on the outside of case 24 for easy access by an operator. Case 24 also includes an electrode compartment 36 which is enclosed by a lid 38 which is mounted to the case by hinges (not shown). A friction-type releasable latch including pins holds lid 38 closed when defibrillator 22 is not in use. Finger-receiving recess 31 in lid 38 is grasped to open the lid and access the electrode compartment 36. An electrode connector 40, speaker 41 and diagnostic display panel 43 are located on case 24 within electrode compartment 36. Diagnostic display panel 43 includes a visual "call for Service" indicator light, a "Check 9 Volt Battery" indicator light, a "Check 12 Volt Battery" indicator light and a "Power" indicator light.

Defibrillator electrodes 50, as illustrated in FIG. 1, each include a polymer backing layer 52, and a patient-engaging layer 54 of conductive adhesive which overlays the backing layer. In the preferred embodiment of the present invention, backing layer 52 is a flexible polymeric foam. Conductive adhesives for electrode use are well-known and commercially available, such as Ludlow Technical Products' conductive hydrogel. A current-dispersing flexible conductive sheet (not shown) is preferably located between backing layer 52 and patient-engaging layer 54 so as to disperse current over conductive adhesive layer 54. The conductive sheet need not be the same size as the electrode and is preferably a homogeneous, solid, thinly deposited metallic substance, or a conductive ink. Meshes or patterns of conductive adhesives or inks may also be used.

Insulated lead wires 56 extend from each electrode 50, and have a first end connected within each electrode 50 to its conductive sheet and a second end connected to a connector 58. Connector 58 is configured to releasably mate with electrode connector 40 in electrode compartment 30, as illustrated. Electrodes 50 are sealed within a polymer or polymer-metal laminate package 60. Lead wires 56 and connector 58 extend from package 60.

A first embodiment of a pair of electrodes 50 to be provided within package 60 is shown in FIG. 2 and 3. The package design of FIG. 1 illustrates electrodes 50 folded against one another and provided within package 60. As shown in FIG. 2, each electrode 50 includes backing layer 52, patient-engaging layer 54 of conductive adhesive, a conductive sheet 53 (illustrated in FIG. 3) between layers 52 and 54, and a liner 61. Liner 61 can comprise any conventional lining material such as plastic sheeting or treated papers. Both electrodes 50 may be provided together on a single liner sheet; however, for reasons set out below, other compensations would be necessary.

A lead wire 56 connects with each electrode 50. Specifically, lead wire 56 extends partially within each electrode 50, preferably between backing layer 52 and conductive adhesive layer 54. A terminal 62 is provided at the end of lead wire 56 within each electrode 50 for preferably connecting the conductive wire of lead wire 56 to conductive sheet 53. Otherwise, lead wire 56 may directly conduct current to conductive adhesive layer 54.

In accordance with the present invention, each terminal 62 preferably extends through backing layer 52 so as to provide a conductor 63 at the surface of backing layer 52. Conductive connector 64 preferably comprises a metal foil or a fine wire which can be folded for packaging and easily torn or broken, the reasons for which will be evident from the description below. Moreover, connector 64 can be conventionally electrically connected to conductors 63 by conductive adhesive, heat bonding solder, or the like. Preferably, conductors 63 and conductive connector 64 are positioned and arranged, such as that illustrated in FIG. 2, so that when electrodes 50 are to be packaged within package 60, they can be folded against on another by a fold line 65 bisecting conductive connector 64. By this arrangement, an electrical circuit can be completed between lead wires 56 through terminals 62, conductors .63, and connecting conductor 64. Also preferably provided is a strip of tear resistant material 66 that is more preferably provided at about the mid-point of connecting conductor 64 and which extends transverse to the direction of connector 64. Tear resistant strip 66 may comprise a plastic, paper, or other non-conductive material which is tear resistant as compared to the material of conductive connector 64.

Referring back to FIG. 1, electrodes 50 are folded toward on another along fold line 65 and positioned within a pouch type package 60 that can be conventionally made either of tow sheets connected together or a single sheet folded and sealed at its edges 67. One of sealed edges 67 accommodates the passage of lead wires 56 from package 60 by forming a small opening through the edge. Preferably also, edge 67 also accommodates passage of a portion of tear resistant strip 66 from the interior of package 60 to the outside of package 60. A tear line 69 is also provided along package 60 dividing interior portion 68 of package 60 from the rest of the inside of the package that is inhabited by the folded pair of electrodes. Tear line 69 may be facilitated by a line of weakening or other means for controlling package opening along tear line 69. Conductive connector 64 preferably extends within package 60 sufficiently from each electrode 50 into package interior portion 68 so that tear resistant strip also lies completely within interior portion 68.

To open package 60, a user is instructed to tear the package along tear line 69. The portion of tear resistant strip 66 extending from package 60 can be used for grabbing by the user to open the package. Otherwise, the user would simply rip along tear line 69. In tearing open package 60 along tear line 69, conductive connector 64 will be likewise torn or broken. Thus, by opening package 60, the circuit between leadwires 56 of electrode 50 within package 60 will be broken. The provision of tear resistant strip 66 not only provides an extension for grabbing to begin opening the package 60, it also ensures that conductive connector 64 will be broken during a tearing operation. As a result of this construction, the presence of an unbroken conductive connector 64 and the subsequent breaking thereof during usage of electrodes 50 can be automatically detected for determining the presence or absence of fresh electrodes 50.

A second embodiment of a pair of electrodes 200 is illustrated in FIGS. 4 and 5. Specifically, the construction of each electrode 200 is preferably the same as that described above including a backing layer, a patient-engaging conductive adhesive layer, and a current dispersing flexible conducting sheet therebetween. Likewise, lead wires 56 extend partially within electrodes 200 between the backing layer and the conductive adhesive layer of each electrode 200 and are preferably connected with the conductive sheets at terminals 202. Terminals 202 similarly provide conductors 204 at the surface of the backing layers of each electrode 200. Electrodes 200 are each provided on separate liners 206. As with the previous embodiment, a single liner could be used. A pair of electrodes 200 are connected together by a conductive connector 208 specifically connected from one conductor 204 of one electrode 200 to conductor 204 of another electrode 200. Again, conductor 204 can be conventionally connected to conductive connector 208 by conductive adhesive, heat bonding, solder or the like. Conductive connector 208 preferably comprises a thin metal foil. Moreover, in accordance with this embodiment, conductor connector 208 includes an extension portion 209 that is preferably integrally formed with conductive connector 208. Portion 209 extends transversely from conductive connector 208 preferably at about center fold line 210, and extends substantially further than the edge of liners 206.

In order to provide electrodes 200 within a package 212, shown in FIG. 5, the construction and arrangement shown in FIG. 4 is folded substantially on fold line 210 so that electrodes 200 are positioned back to back with liners 206 against one another. Package 212 can be a conventional construction pouch having edge seals 214 around its periphery. Electrodes 200 are received within an electrode interior portion 216 which is divided from an interior portion 218 by a tear line 220. As above, lead wires 56 are accommodated through one of edge seals 214. Likewise, portion 209 of conductive connector 208 preferably extends sufficiently that it extends through the same edge seal to facilitate opening of the package. Conductive connector 208 preferably extends within the package sufficiently from each electrode 200 into package interior portion 218 so that portion 209 of conductive connector 208 lies within interior package portion 218.

Then, to open package 212, a user would simply grasp the package at or near extension portion 209 and tear the package open along tear line 220. Extension portion 209 ensures that tearing along tear line 220 by grasping extension point 209 will tear through conductive connector 208 and break the circuit between lead wires 56. As above, the function of making and generating the circuit completed by conductive connection 208 and terminals 202 between lead wires 56 can be monitored by defibrillator 22, as described generally below, for determining the presence of fresh electrodes.

Figure 7:
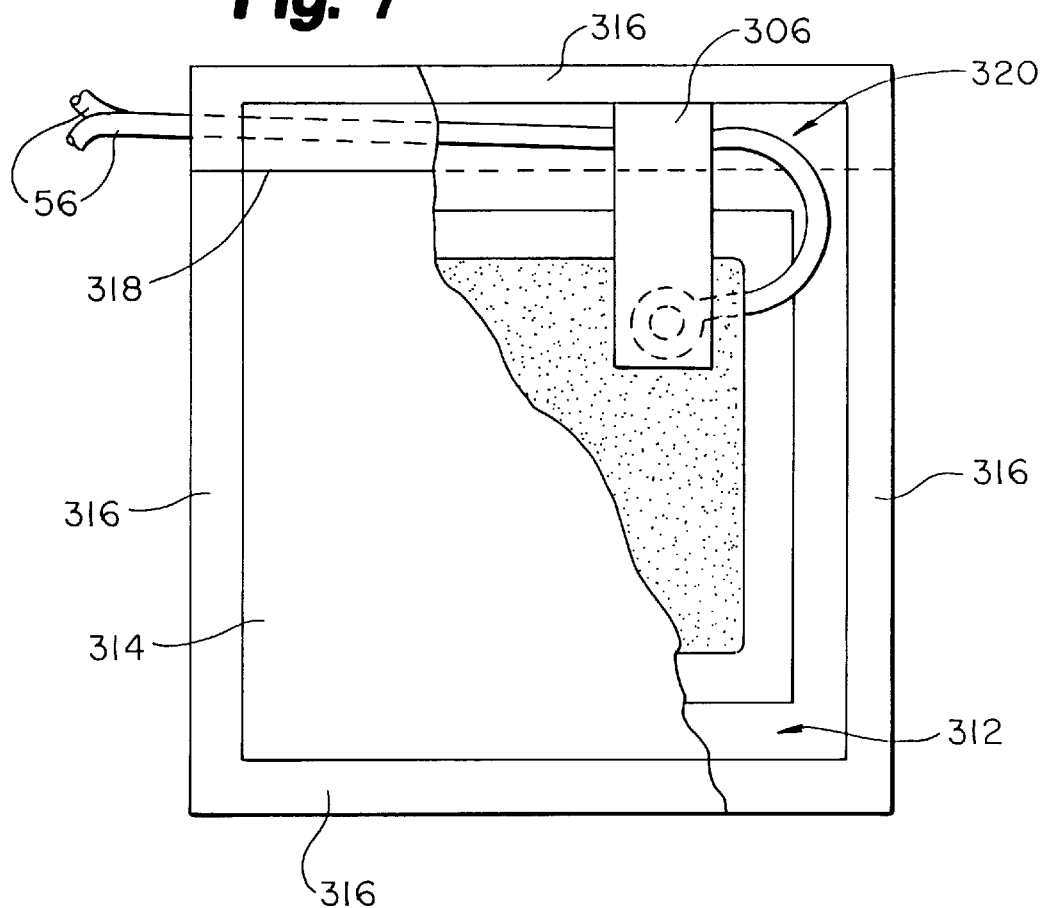
FIG. 7 is a plan view of the electrodes of FIG. 6 folded together and provided within a package shown partially torn away.

Yet another embodiment is illustrated in FIGS. 6 and 7. Electrodes 300 are provided which are similarly constructed as the aforementioned embodiments, including a backing layer, a conductive adhesive layer and a conductive sheet therebetween. Leadwires 56 are preferably connected with the conductive sheet's between the backing layer and the conductive adhesive layer by terminals 302. Each terminal 302 also preferably provides a conductor 304 at the surface of the backing layer of each electrode 300. A pair of electrodes 300 are connected together by a conductive connector 306, specifically connected at each end to a conductor 304 of a terminal 302. Again, conventional connection means can be used, such as conductive adhesives, heat bonding, solder or the like. Conductive connector 306 may comprise a thin foil, a fine wire, or the like, by preferably comprises a thin foil. Each electrode 300 is also preferably provided on a separate liner 308. A fold line 310 substantially bisects the conductive connector 306 so that electrodes 300 can be folded back to back with liners 308 against one another. Conductive connector 306 completes an electrical circuit for connecting lead wires 56 by way of terminals 302 and conductors 304.

Electrodes 300 are positioned within an electrode receiving space 312 of package 314 which may be conventionally constructed with sealed edges 316. The interior of the package is divided by a tear line 318 into electrode receiving portion 312 and an interior portion 320.

In accordance with this embodiment, it is important that at least one of lead wires 56 should be properly threaded within the package so as to exit package 314 at one of its edge seals 316 from within interior portion 320 of package 314. Moreover, conductive connector 306 forms a loop that extends within interior portion 320 of package 314. Preferably, both lead wires 56 pass through the loop defined by conductive connector 306 when the electrodes are positioned back to back as folded along fold line 310. More particularly, lead wires 56 pass between conductive connector 306 and an edge of a liner 308. Furthermore, conductive connector 306 is sufficiently long so that when the electrodes are folded back to back, conductive connector 306 forms the loop so as to facilitate both lead wires 56 within interior portion 320. By this embodiment, package 314 can be easily opened along tear line 318 by grasping lead wires 56 where they exit package 314 at edge seal 316. Then, tearing the package open along tear line 318 will also tear or break conductive connector 306. Lead wires 56, in this case, act as a tear strip facilitating easy opening of package 314. This construction is advantageous in that a single action opens the electrode package, breaks the electrical circuit, and removes the electrodes from the package. As above, the function of making and breaking the electrical circuit completed by connector 306 between lead wires 56 can be monitored, as set out below, for determining the presence of fresh electrodes 300.

As an alternative construction to each of the above-described embodiments, liners 61, 206, and 308 could instead comprise a single liner to which both electrodes 50, 200, and 300 respectively, are adhered. To do this, the liners would also be folded to position the electrodes within the respective packages. However, in order to provide that conductive connectors, 64, 208 and 306, respectively, extend across tear lines 69, 220 and 318 respectively, the conductive connectors must be of sufficiently greater length than the distance between the electrodes on a single liner so that when the single liners are folded, the conductive connectors will form a loop that extends sufficiently away from the folded edge of the single liner. It should be noted hat the present invention is equally applicable to solid liners and to liners having a plurality of perforation formed therein.

Figure 8:
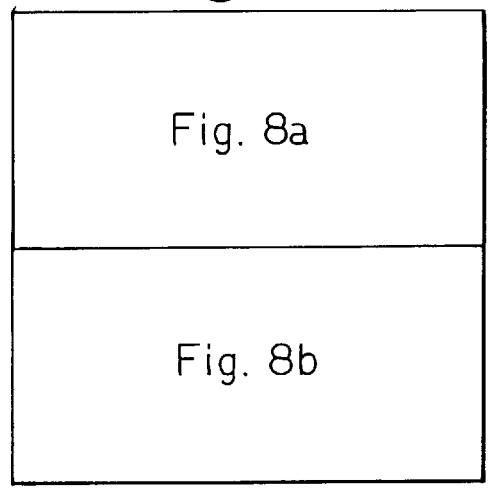
FIG. 8 is a block diagram of an electrical system of an AED.
Figure 8A:
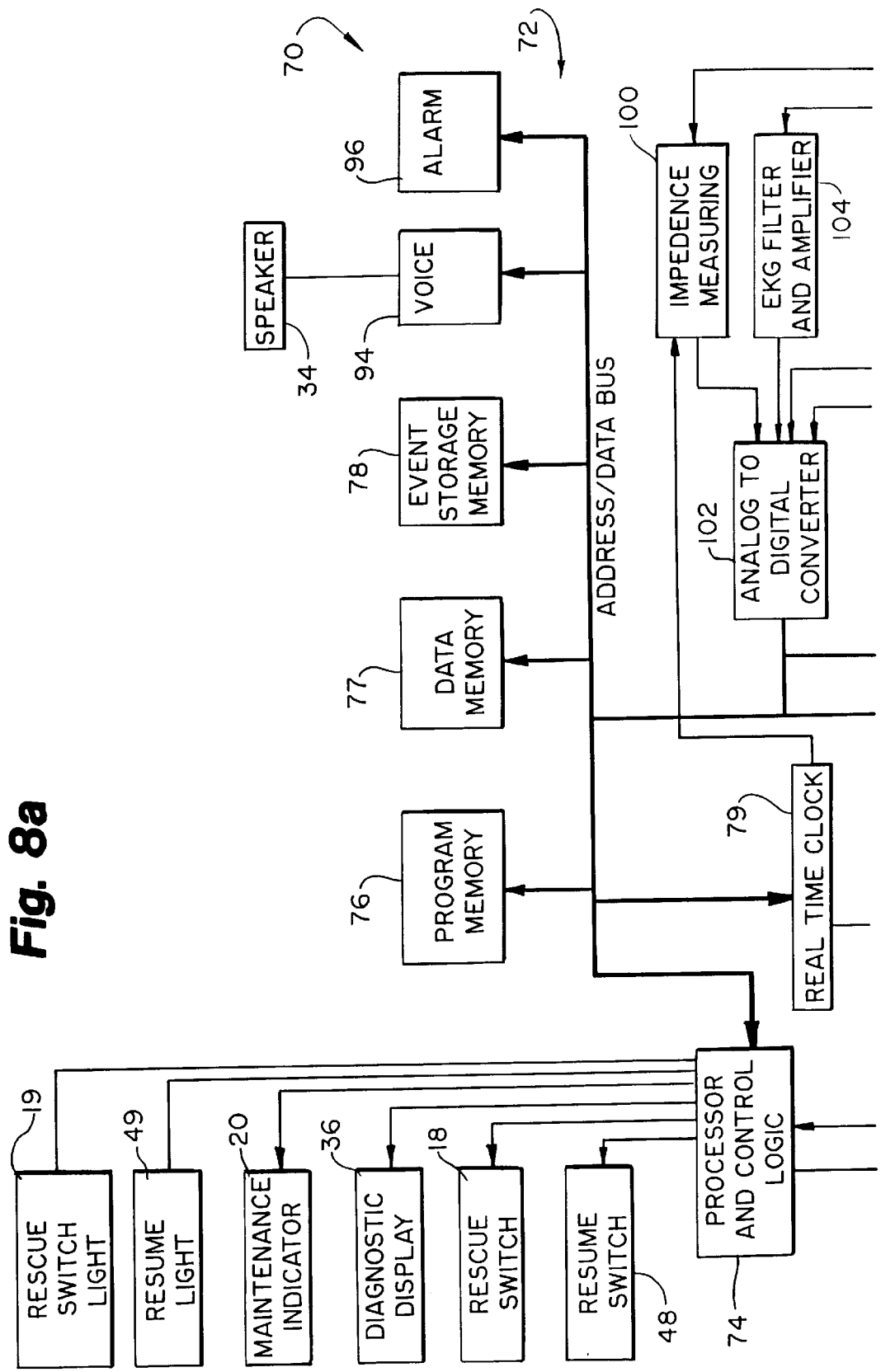
Figure 8B:
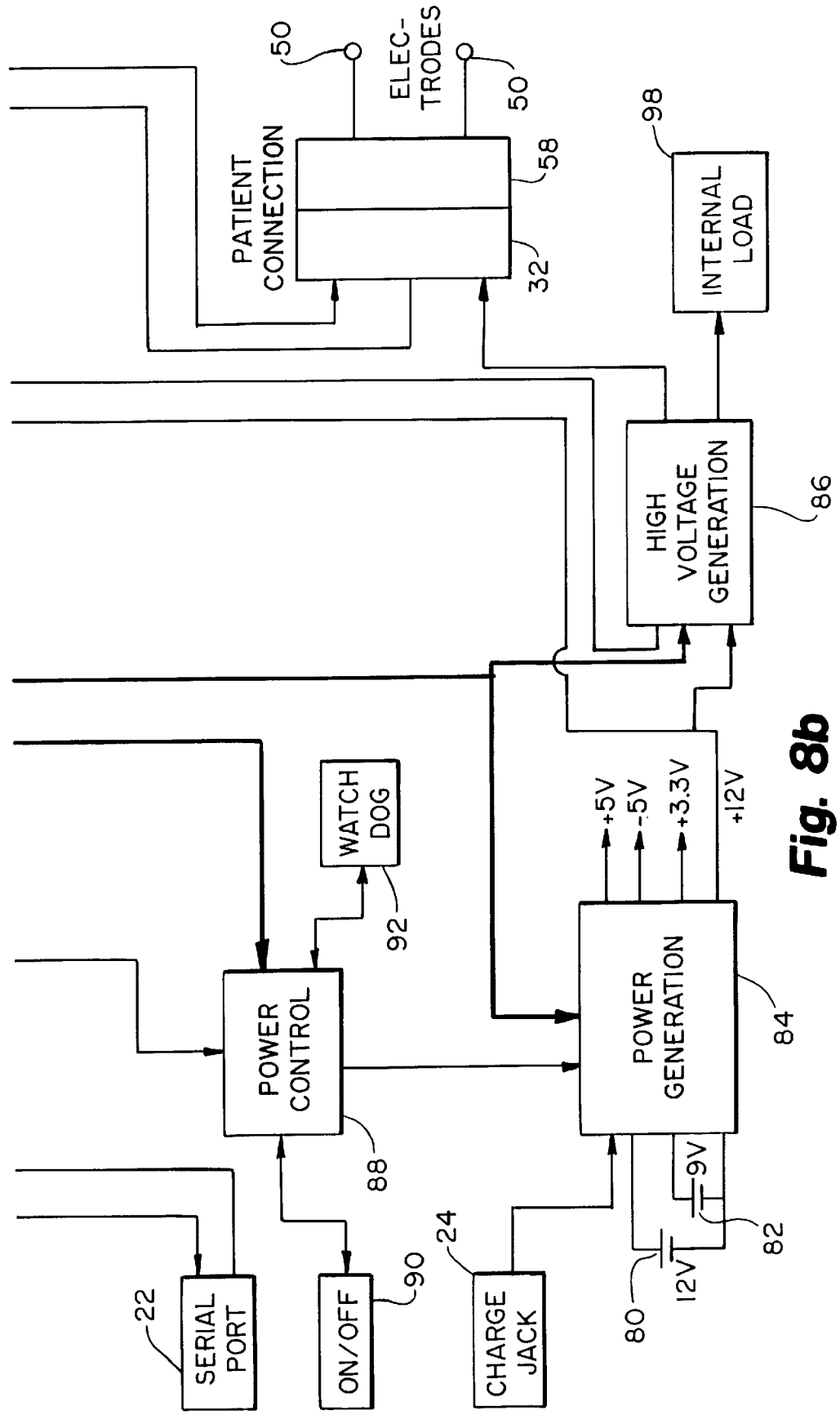

FIG. 8 is a block diagram of electrical system 70 of defibrillator 22. The overall operation of defibrillator 22 is controlled by a digital microprocessor-based control system 72 which includes a processor 74 interfaced to program memory 76, data memory 77, event memory 78 and real time clock 79. The operating program executed by processor 74 is stored in program memory 76. Electrical power is provided by a rechargeable twelve volt lead-acid cartridge battery 80 and a nine volt battery 82 which are removably positioned within the battery compartment and connected to power generation circuit 84. Charging port 25 is coupled to power generation circuit 84, enabling twelve volt battery 80 to be connected to a twelve volt vehicle battery (not shown) or a 120 VAC charger (also not shown) and recharged while mounted within defibrillator 22. Alternatively, battery 80 can be removed from defibrillator 22 and charged in a stand-alone charger (not shown).

Power generation circuit 84 is also connected to lid switch 90, watch dog timer 92, real time clock 79 and processor 74. Lid switch 90 is a magnetic read relay switch in one embodiment, and provides signals to processor 74 indicating whether lid 38 is open or closed. Data communication port 32 is coupled to processor 74 indicating whether lid 38 is open or closed. Data communication port 32 is coupled to processor 74 for two-way serial data transfer using an RS-232 protocol. Rescue switch 28, maintenance indicator 30, the rescue switch light, resume switch, indicator lights of the diagnostic display panel, the voice circuit 94 and piezoelectric audible alarm 96 are also connected to processor 74. Voice circuit 94 is connected to speaker 41. In response to voice prompt control signals from processor 74, circuit 94 and speaker 41 generate audible voice prompts.

High voltage generation circuit 86 is also connected to and controlled by processor 74. Circuits such as 86 are generally known, and. disclosed, for example, in the commonly assigned Persson et al. U.S. Pat. No. 5,405,361, which is hereby incorporated by reference. In response to charge control signals provided by processor 74, high voltage generation circuit 86 is operated in a charge mode during which one set of semiconductor switches (not separately shown) cause a plurality of capacitors (also not shown), to be charged in parallel to the 12V potential supplied by power generation circuit 84. Once charged, and in response to discharge control signals provided by processor 74, high voltage generation circuit 86 is operated in a discharge mode during which the capacitors are discharged in series by another set of semiconductor switches (not separately shown) to produce the high voltage defibrillation pulses. The defibrillation pulses are applied to the patient through electrode connector 40 which is connected to the high voltage generation circuit 86.

Impedance measuring circuit 100 is connected to electrode connector 40 and real time clock 79, and is interfaced to processor 74 through analog-to-digital (A/D) converter 102. Impedance measuring circuit 100 receives a clock signal having a predetermined magnitude from clock 79, and applies the signal to electrodes 50, for example, through connector 40. The magnitude of the clock signal received back from electrodes 50 through connector 40 is monitored by impedance measuring circuit 100. An impedance signal representative of the impedance present across electrode connector 40 is then generated by circuit 100 as a function of the ration of the magnitudes of the applied and received clock signals (i.e., the attenuation of the applied signal). For example, if electrode 50 within an unopened package 60 are connected by conductive connector 64 and connector 58 is properly connected to connector 40 on defibrillator 22, a relatively low resistance (e.g., less than about 10 ohms) should be present across connector 40. If package 60 is opened, connector 58 is not properly connected to connector 40, or the electrodes are not properly positioned on the patient, a relatively high resistance (e.g., greater than about two hundred fifty ohms) will be present across connector 40. The resistance across connector 40 will be between about twenty-five and two hundred fifty ohms when fresh electrodes 50 are properly positioned on the patient with good electrical contacts. It should be noted that these resistance values are given as exemplary ranges and are not meant to be absolute ranges. The impedance signal representative of the impedance measured by circuit 100 is digitized by A/D converter 102 and provided to processor 74.

Figure 9:
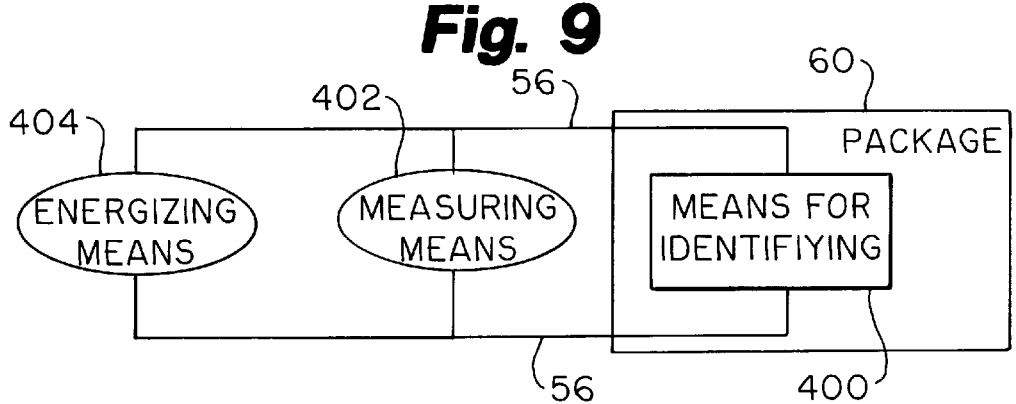
FIG. 9 is a schematic view of a general electrode detector circuit.

With reference to FIG. 9 a general concept is schematically illustrated for detecting the presence of pediatric electrodes.

An electrode containing package 60 is schematically illustrated in FIG. 9, however, it should be understood that any electrode packages in accordance with the present invention may be used. Within package 60 a means for identifying a pair of electrodes as pediatric electrodes is shown at 400. Patient identification element 400 is preferably provided as part of an electrical circuit that includes a measuring means 402 and an energizing means 404 used for stimulating the circuit. Preferably, the circuit utilizes lead wires 56 for connecting to identification element 400. Measuring means 402 functions as a part of the process of identifying electrodes 50 as pediatric electrodes as a result of the energizing of the circuit by means 404. Based upon a measured response, i.e., a signal or a change in the current or voltage, processor 74 can determine if electrodes 50 are pediatric electrodes. When the processor 74 detects the presence of pediatric electrodes, it may select a different set of voice prompts that are specifically suited to a pediatric patient and/or it may select a pediatric dosage of electricity for the therapeutic shock. For example, processor 74 may select a predetermined pediatric shock treatment protocol consisting of a series of defibrillation shocks with energies of 50, 100, and 200 Joules. For adult patients the predetermined shock treatment protocol may consist of a series of defibrillation shocks with energies of 200, 300, and 360 Joules.

In one embodiment of the present invention, identification element 400 is an integral part of conductive connector 64, 208, or 306, which is connected between lead wires 56. Identification element 400 may also be otherwise incorporated within package 60. Alternatively, a separate set of wires may be provided for connecting identification element 400. Furthermore, identification element 400 may be separately provided such that the separate set of wires does not have to be incorporated into the package.

Figure 10:
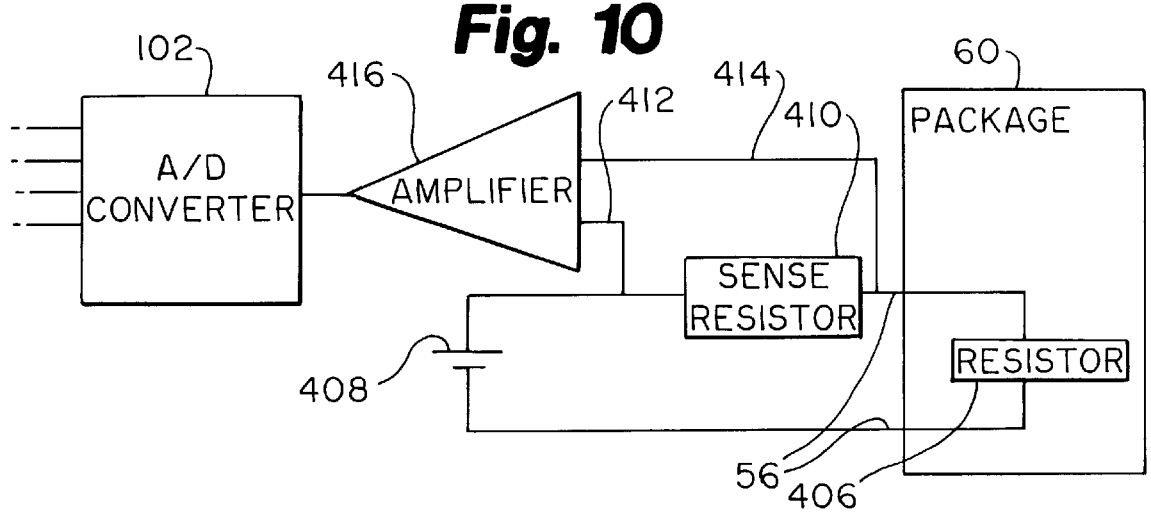
FIG. 10 is a schematic view of detector circuit including a passive identification element.

An example of a specific circuit that can be incorporated within the circuit illustrated in FIG. 9 is shown in FIG. 10. This circuit comprises an implementation of the general concept described above for detecting the presence of pediatric electrodes based on the presence of a passive electrical component as identification element 400. Specifically, one example of a passive component is a resistor 406 of a predetermined resistance. The value of resistance 406 is selectively chosen to indicate that electrodes 50 are electrodes intended for a specific type of patient. Based on measured value of resistor 406 processor 74 selects an appropriate predetermined shock treatment protocol. For example, processor may select a predetermined pediatric shock treatment protocol consisting of a series of defibrillation shocks with energies of 25, 50, and 100 Joules.

In the FIG. 10 circuit, the energizing means specifically comprises a voltage source 408. The measuring means comprises a sense resistor of a known value, and means for measuring the voltage drop across sense resistor 410 comprising lines 412 and 414 connected through an amplifier 416 to analog to digital converter 102 and processor 74. Given that the voltage of voltage source 408 is known and the value of sense resistor 410 is known, the value of the resistance across electrodes 50 can be calculated using standard circuit analysis techniques. Solving for 406 the following equation is obtained.

$$R_E = R_S\left(\frac{v}{v_s} - 1\right)$$

Where, $R_E$ is the electrode resistance; $R_S$ is the sense resistor 410 resistance value; v is the voltage of voltage source 408; and $v_S$ is the voltage drop measured across the sense resistor 410.

Thus, having a resistor 406 with a predetermined value representing a pediatric electrode; the presence of a pediatric electrode can be determined by processor 74 based simply on the signal which it receives from analog to digital converter 102 which is in turn based on the voltage drop across sense resistor 410. Once processor 74 detects the presence of pediatric electrodes based on the voltage drop, it may select a different set of voice prompts that are specifically suited to a pediatric patient and/or it may select a pediatric dosage of electricity for the therapeutic shock.

Alternately, passive components other than a resistor may be utilized. Element 406 may instead comprise a capacitive element or an inductive element where the value may be determine by well known and understood methods of electronically measuring capacitance, resistance, and inductance.

Figure 11:
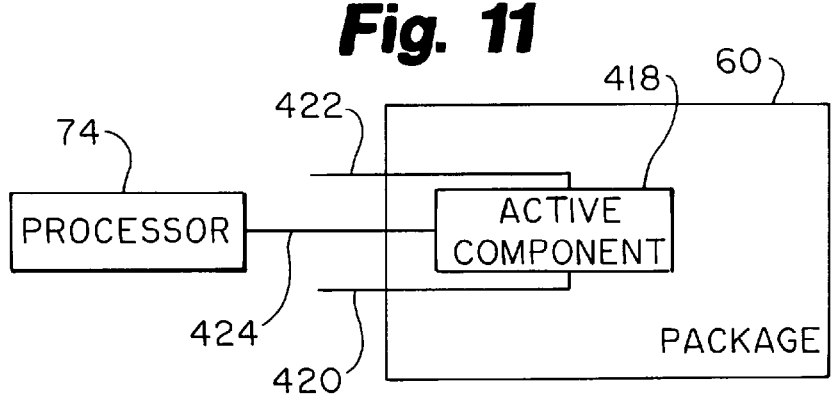
FIG. 11 is a schematic view of detector circuit including an active identification element.

Another example of a specific circuit that can be incorporated within the circuit of FIG. 9 is shown in FIG. 11 and comprises the general concept of FIG. 9 but is based on the presence of an active component as the identification element 400. Specifically, an active component 418 is provided within package 60 and may be provided separately from the conductive connector element of the electrode pair or may be integrally incorporated within the conductive connector. Energizing means 404 comprises a voltage source represented by lines 420 and 422. Line 424 connects active component 418 to processor 74, preferably by way of analog to digital converter 102. This circuit works on the basis that when active component 418 is connected to a voltage source, specific data is generated by active component 418 indicating the presence of pediatric electrodes. The data travels via line 424 to processor 74 which can then determine whether or not the electrodes within package 60 are pediatric electrodes.

One example of an active component 418 is a read only memory chip, such as the Dallas chip DS 2400, commercially available from Dallas Semiconductor, Inc. Another example is a digital sensor identifier, which provides a specific signal as the data output upon connection to the voltage source. Other known active components could also be used without departing from the spirit or scope of the present invention.

AED Operation with Circuit Detectable Pediatric Electrodes

Identification element 400 may be used to communicate the presence of electrodes intended for patients of a specific weight range. The steps for the operation of AED 22 are listed below:

1) When AED 22 is activated processor 74 reads identification element 400 and determines the weight range of the patient.
2) Processor 74 crafts the electrotherapy to best treat the patient based on the patient's weight range.
3) The treatment delivery system of AED 22 is charged in preparation for delivering the electrotherapy.
4) When rescue switch 28 is activated AED 22 delivers the electrotherapy to the patient.

Selecting the appropriate electrotherapy may include selecting the shape or type of shock waveform, selecting the leading edge voltage of the defibrillation shock, selecting the energy of the defibrillation shock, and selecting the duration of the defibrillation shock.

As mentioned above crafting the electrotherapy may include selecting the energy of the defibrillation shock. When ventricular fibrillation is present in a pediatric patient, a weight related energy dose of 2 J/Kg (1 J/lb) is often used. In an escalating energy shock protocol the energy dose is doubled for the second and third shocks if the first shock was unsuccessful. For example, if the patient weight is greater than zero and less than 10 Kg, AED 22 will prepare to deliver an escalating series of rescue shocks with energies of 10, 20, and 40 Joules. If the patient weight is greater than or equal to 10 Kg and less than or equal to 20 Kg, AED 22 will prepare to deliver a series of rescue shocks with energies of 30, 60, and 120 Joules. If the patient weight is greater than or equal to 20 Kg and less than or equal to 40 Kg, AED 22 will prepare to deliver a series of shocks with escalating energies of 60, 120, and 240 Joules. If the patient weight is greater than 40 Kg (e.g. adult patient), AED 22 will prepare to deliver a series of shocks with escalating energies of 200, 300, and 360 Joules.

It should be understood that in the previous example, other energy levels may be selected without departing from the spirit or scope of this invention. Factors other than patient weight may also be used to selected appropriate shock energies. Patient age and the chest size of the patient may be used as indicators of the appropriate shock energy required. In this case identifying means 400 would be adapted to correspond to the patients age or chest size.

Also, crafting the electrotherapy may include selecting the waveform of the defibrillation shock. For example, if the patient weight is greater than zero and less than 20 Kg, AED 22 may deliver a damped sine waveform. If the patient weight is greater than or equal to 20 Kg and less than or equal to 40 Kg, AED 22 may deliver a monophasic truncated exponential waveform. If the patient weight is greater than 40 Kg, AED 22 may deliver a biphasic truncated exponential waveform. It should be understood that the weight ranges and waveforms described above are for illustration only. Other weight ranges and waveforms may be selected without departing from the scope or spirit of this invention.

Finally, as mentioned above crafting the waveform may include adjusting the leading edge voltage of the defibrillation shock. If the defibrillation shock is of a biphasic type, crafting may include adjusting the lead edge of the first phase and the second phase of the biphasic defibrillation shock.

Figure 12:
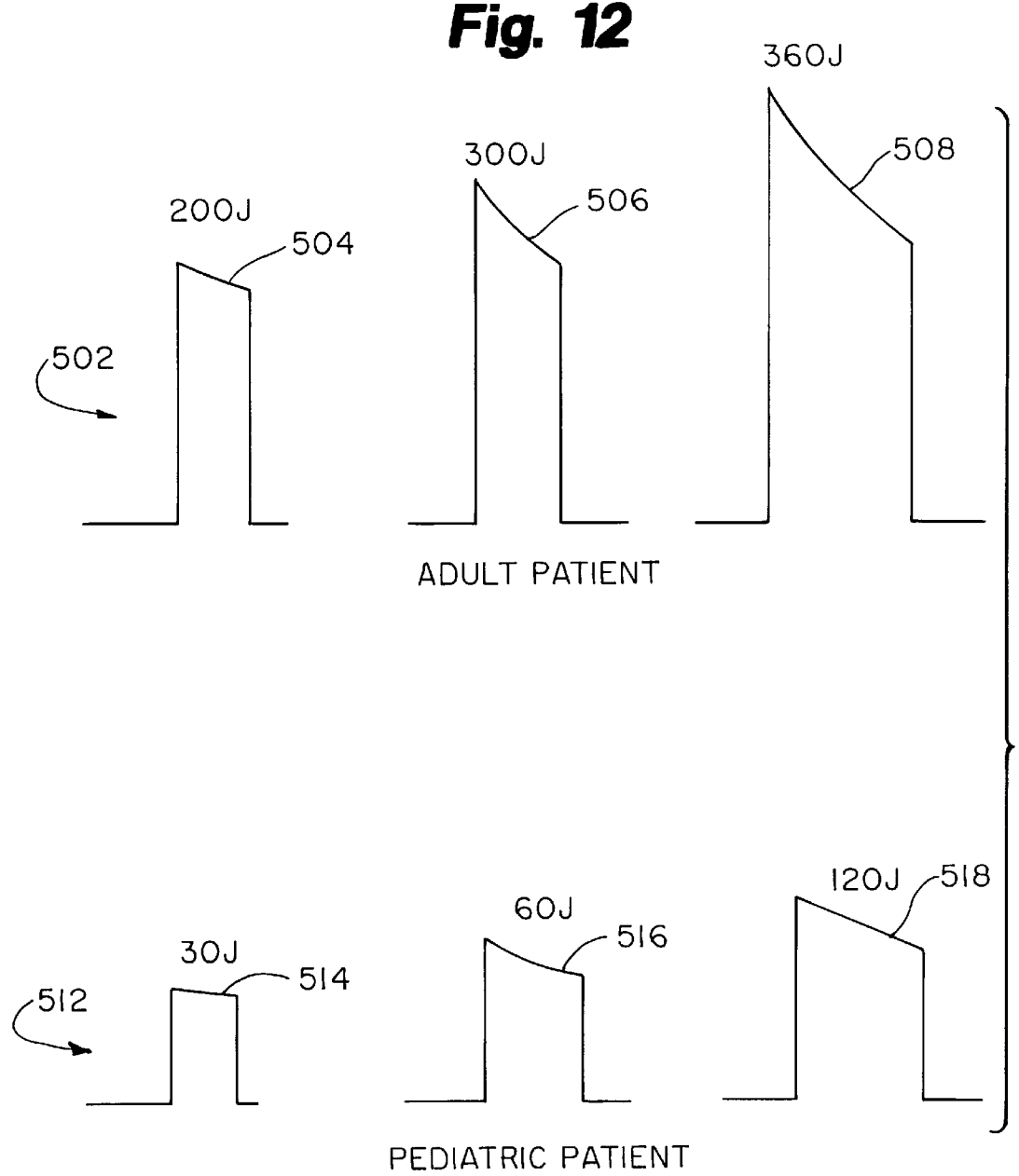
FIG. 12 is a graphical representation of monophasic shock treatment protocols for both adult and pediatric patients.

FIG. 12 illustrates example shock treatment protocols for both adult and pediatric patients. Adult shock treatment protocol 502 consists of three monophasic shock pulses with escalating energies. First shock 504 has an energy of 200 Joules, second shock 506 has an energy of 300 Joules, and third shock 508 has an energy of 360 Joules.

Pediatric shock treatment protocol 512 also consists of three monophasic shock pulses as shown in FIG. 12. First shock 514 has an energy of 30 Joules, second shock 516 has an energy of 60 Joules, and third shock 518 has an energy of 120 Joules.

Figure 13:
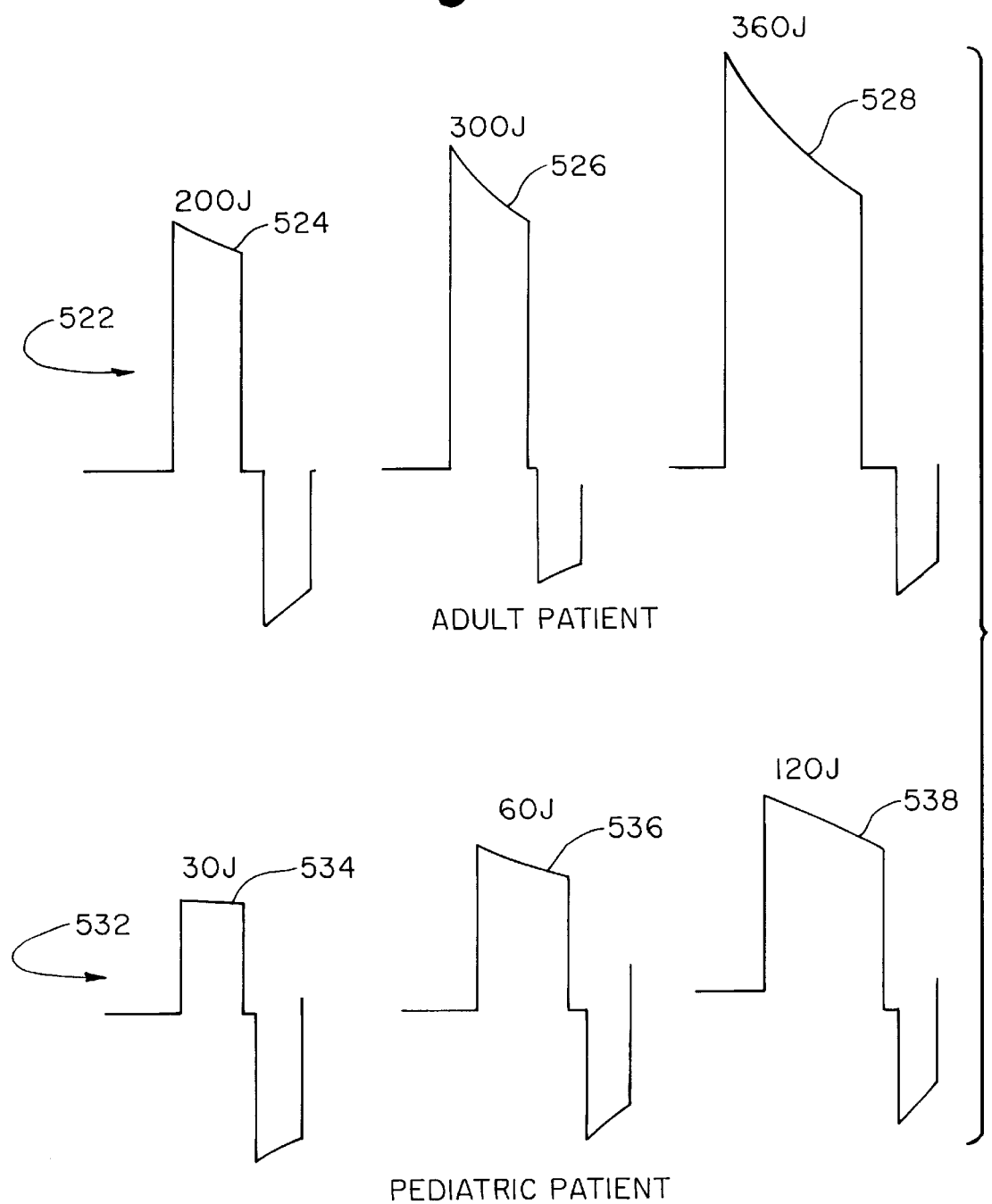
FIG. 13 is a graphical representation of biphasic shock treatment protocols for both adult and pediatric patients.

FIG. 13 includes two examples of biphasic shock treatment protocols. Adult shock treatment protocol 522 consists of three biphasic shock pulses with escalating energies. First shock 524 has an energy of 200 Joules, second shock 526 has an energy of 300 Joules, and third shock 528 has an energy of 360 Joules.

Pediatric shock treatment protocol 532 also consists of three biphasic shock pulses as shown in FIG. 12. First shock 534 has an energy of 30 Joules, second shock 536 has an energy of 60 Joules, and third shock 538 has an energy of 120 Joules.

As will be readily appreciated by those skilled in the art, other pediatric-determined energy sequences may also be appropriate. For example, shock energy sequences of 30 J, 30 J, 60 J, or 60 J, 60 J, 120 J may selected for smaller children (e.g. 0<patient age≦8 years). For older children (e.g. 8<patient age≦12 year) example shock energy sequences would include 60 J, 60 J, 120 J, or 60 J, 120 J, 120 J. Other shock energies may also be selected without departing from the spirit or scope of this invention. For example, shock energies of 25 Joules, 30 Joules, 50 Joules, 60 Joules, 100 Joules, 120 Joules, 200 Joules, and 240 Joules may be selected.

Referring again to FIG. 10, a specific example of how AED 22 determines the weight of the patient is included below. The value of resistor 410 is determined using the method described previously. This resistance value converted is to a digital signal by analog-to-digital converter 102. Processor 74 reads the digital signal from analog-to-digital converter 102. Processor 74 uses the digital signal to determine the weight range appropriate to the patient. Processor 74 then performs a decision making process to select an predetermine electrotherapy regiment which is appropriate for patients in that weight range.

Although the present invention has been described with reference to preferred embodiments, workers skilled in the art will recognize that changes may be made in form and detail without departing from the spirit or scope of the present invention.

What is claimed is:

1. A method of performing external defibrillation using an automated external defibrillator (AED), the steps comprising:

measuring a patient parameter from a patient identification element;

using said measured parameter to configure said AED to output a predetermined shock treatment protocol;

said predetermined shock treatment protocol being a series of low energy shocks appropriate for pediatric patients.

2. A method of performing external defibrillation using an automated external defibrillator (AED), the steps comprising:

measuring a patient parameter from a patient identification element;

using said measured parameter to configure said AED to output a predetermined shock treatment protocol; and said predetermined shock treatment protocol being a series of low energy shocks.

3. A method of performing external defibrillation using an automated external defibrillator (AED), the steps comprising:

measuring a patient parameter from a patient identification element;

using said measured parameter to configure said AED to output a predetermined shock treatment protocol; and said predetermined shock treatment protocol being a series of escalating energy shocks.

4. A method of performing external defibrillation using an automated external defibrillator (AED), the steps comprising:

measuring a patient parameter from a patient identification element;

using said measured parameter to configure said AED to output a predetermined shock treatment protocol; and said predetermined shock treatment protocol being a series of defibrillation shocks with energies of 60 Joules, 120 Joules, and 240 Joules.

5. A method of performing external defibrillation using an automated external defibrillator (AED), the steps comprising:

measuring a patient parameter from a patient identification element;

using said measured parameter to configure said AED to output a predetermined shock treatment protocol; and said predetermined shock treatment protocol being a series of defibrillation shocks with energies of 30 Joules, 60 Joules, and 120 Joules.

6. An external defibrillation system comprising:

two electrodes electrically connected to one another by an interconnection circuit and adapted to make electrical contact with the exterior of a patient;

an AED with electrode terminals configured for electrical interconnection with said two electrodes; and identification element representative of the type of patient being rescued within said interconnection circuit.

7. The defibrillation system of claim 6, wherein said identification element comprises a passive element within an interconnection circuit of a packaged pair of electrodes.

8. The defibrillation system of claim 7, wherein said passive element is a resistor.

9. The defibrillation system of claim 7, wherein said passive element is a capacitor.

10. The defibrillation system of claim 7, wherein said passive element is an inductor.

11. The defibrillation system of claim 6 wherein said identification element comprises an active element within an interconnection circuit of a packaged pair of electrodes.

12. The defibrillation system of claim 11, wherein said active element is a read only memory chip.

13. The defibrillation system of claim 11, wherein said active element is a digital sensor identifier.

14. A method of performing external defibrillation using an automated external defibrillator (AED), the steps comprising:

measuring a parameter from an identification element; and using said measured parameter to configure said AED to output a predetermined shock treatment protocol for pediatric patients consisting of a series of low energy shocks.

15. A method of performing external defibrillation using an automated external defibrillator (AED), the steps comprising measuring a parameter from an identification element; and using said measured parameter to configure said AED to output a predetermined shock treatment protocol for pediatric patients consisting of a series of escalating energy shocks.

16. A method of performing external defibrillation using an automated external defibrillator (AED), the steps comprising:

measuring a parameter from an identification element; and using said measured parameter to configure said AED to output a predetermined shock treatment protocol for pediatric patients consisting of a series of escalating energy shocks with energies of 50 Joules, 100 Joules, and 200 Joules.

17. A method of performing external defibrillation using an automated external defibrillator (AED), the steps comprising:

measuring a parameter from an identification element; and using said measured parameter to configure said AED to output a predetermined shock treatment protocol for pediatric patients consisting of a series of escalating energy shocks with energies of 25 Joules, 50 Joules, and 100 Joules.

18. An external defibrillation system comprising:

two electrodes electrically connected to one another by an interconnection circuit and adapted to make electrical contact with the exterior of a patient;

an AED with electrode terminals configured for electrical interconnection with said two electrodes; and a passive element representative of the type of patient being rescued within said interconnection circuit.

19. An external defibrillation system comprising:

two electrodes electrically connected to one another by an interconnection circuit and adapted to make electrical contact with the exterior of a patient;

an AED with electrode terminals configured for electrical interconnection with said two electrodes; and an active element representative of the type of patient being rescued within said interconnection circuit.

20. A method of performing external defibrillation using an automated external defibrillator (AED), the steps comprising:

reading an identification element with a microprocessor; and crafting the electrotherapy to best treat the patient based on the patient's weight range.

21. The method of claim 20, wherein said electrotherapy is appropriate for pediatric patients.

22. The method of claim 20, wherein said electrotherapy is a series of low energy shocks.

23. The method of claim 20, wherein said electrotherapy is a series of escalating energy shocks.

24. The method of claim 20, wherein said electrotherapy is a series of defibrillation shocks with energies selected from the group consisting of 25 Joules and 30 Joules and 50 Joules and 60 Joules and 100 Joules and 120 Joules and 200 Joules and 240 Joules.

25. The method of claim 20, wherein said electrotherapy is a series of defibrillation shocks with energies of 30 Joules, 60 Joules, and 120 Joules.

26. A method of performing external defibrillation using an automated external defibrillator (AED), the steps comprising:

reading an identification element with a microprocessor; and crafting the electrotherapy to best treat the patient based on the patient's age range.

27. The method of claim 26, wherein said electrotherapy is appropriate for pediatric patients.

28. The method of claim 26, wherein said electrotherapy is a series of low energy shocks.

29. The method of claim 26, wherein said electrotherapy is a series of escalating energy shocks.

30. The method of claim 26, wherein said electrotherapy is a series of defibrillation shocks with energies selected from the group consisting of 25 Joules and 30 Joules and 50 Joules and 60 Joules and 100 Joules and 120 Joules and 200 Joules and 240 Joules.

31. The method of claim 26, wherein said electrotherapy is a series of defibrillation shocks with energies of 30 Joules, 60 Joules, and 120 Joules.

32. A method of performing external defibrillation using an automated external defibrillator (AED), the steps comprising:

reading an identification element with a microprocessor; and crafting the electrotherapy to best treat the patient based on the patient's chest size.

33. The method of claim 32, wherein said electrotherapy is appropriate for pediatric patients.

34. The method of claim 32, wherein said electrotherapy is a series of low energy shocks.

35. The method of claim 32, wherein said electrotherapy is a series of escalating energy shocks.

36. The method of claim 32, wherein said electrotherapy is a series of defibrillation shocks with energies selected from the group consisting of 25 Joules and 30 Joules and 50 Joules and 60 Joules and 100 Joules and 120 Joules and 200 Joules and 240 Joules.

37. The method of claim 32, wherein said electrotherapy is a series of defibrillation shocks with energies of 30 Joules, 60 Joules, and 120 Joules.

* * * * *